United States Patent

Noguchi et al.

[11] Patent Number: 6,086,666
[45] Date of Patent: Jul. 11, 2000

[54] PIGMENT FOR SHIELDING OF ULTRAVIOLET RADIATION

[75] Inventors: Tamio Noguchi; Yukitaka Watanabe, both of Iwaki, Japan

[73] Assignee: Merck Patent Gesellschaft mit beschrankter Haftung, Darmstadt, Germany

[21] Appl. No.: 09/109,085

[22] Filed: Jul. 2, 1998

[30] Foreign Application Priority Data

Jul. 3, 1997 [JP] Japan ................................. 9-192021

[51] Int. Cl.[7] .................. C09C 1/01; C09C 3/08; A61K 7/42; A61K 33/30; A61K 33/04

[52] U.S. Cl. .................. 106/425; 106/415; 106/416; 106/417; 424/70.9; 424/59; 424/641; 424/642; 424/709; 424/722; 427/215; 428/363; 428/403

[58] Field of Search ................................. 106/415, 416, 106/417, 425; 424/70.9, 59, 641, 642, 709, 722; 427/215; 428/363, 403

[56] References Cited

U.S. PATENT DOCUMENTS 4,603,047  7/1986  Watanabe et al. ..................... 106/417

FOREIGN PATENT DOCUMENTS 60-231607  of 1984  Japan .
5-279235  of 1992  Japan .

*Primary Examiner*—C. Melissa Koslow
*Attorney, Agent, or Firm*—Millen, White, Zelano & Branigan P.C.

[57] ABSTRACT

An ultraviolet radiation shielding pigment having a high power of shielding of ultraviolet radiation, particularly UV-A, a low cohesive force, and excellent extensibility and adhesiveness as a pigment for cosmetics. A pigment for shielding an ultraviolet radiation which comprises a flaky powder having particle surfaces coated with particles of barium sulfate having an average diameter of 0.1 to 2.0 microns, and with needle crystal particles of zinc oxide having an average major-axis diameter of 0.05 to 1.5 microns, and a process for manufacturing it.

15 Claims, 2 Drawing Sheets

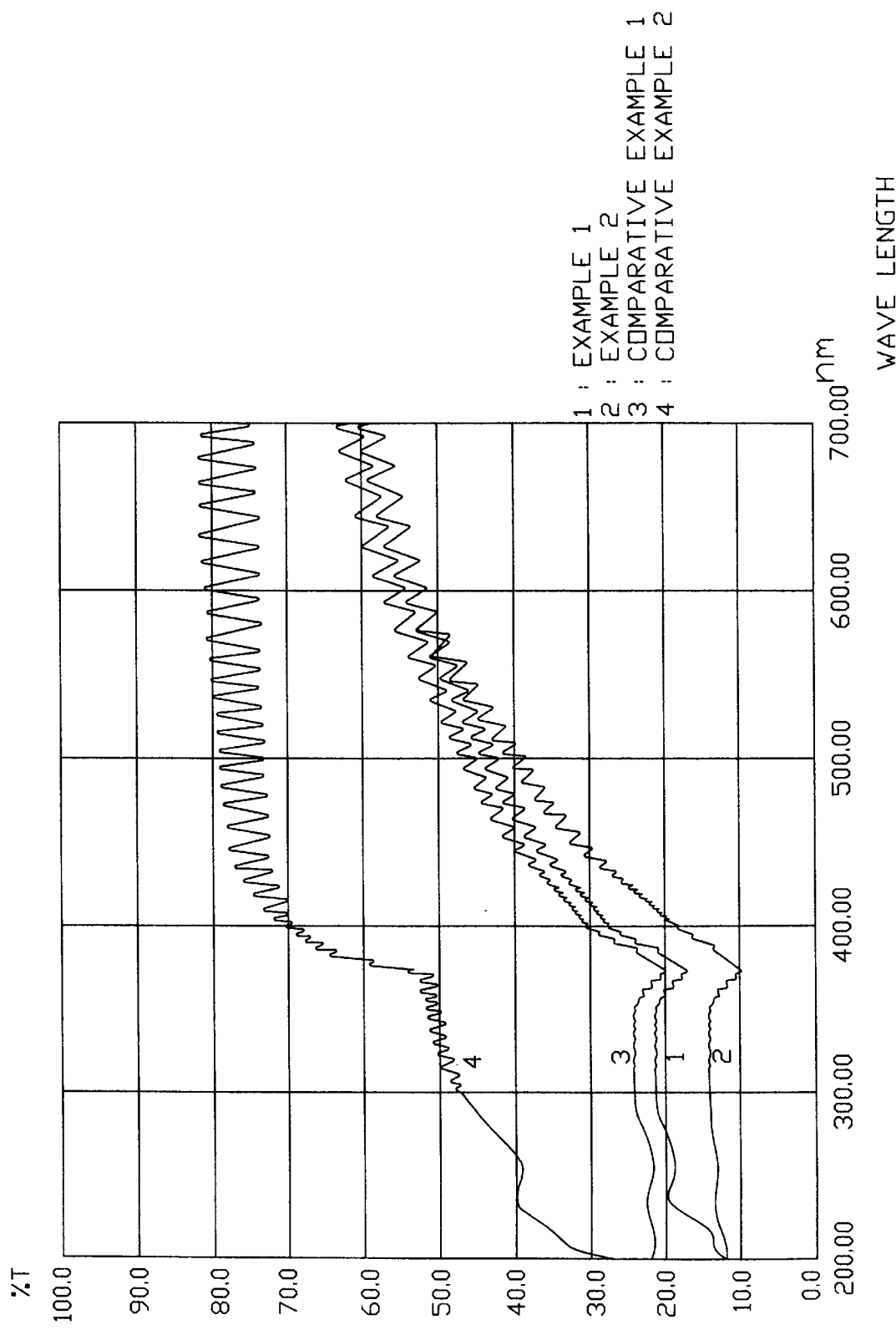

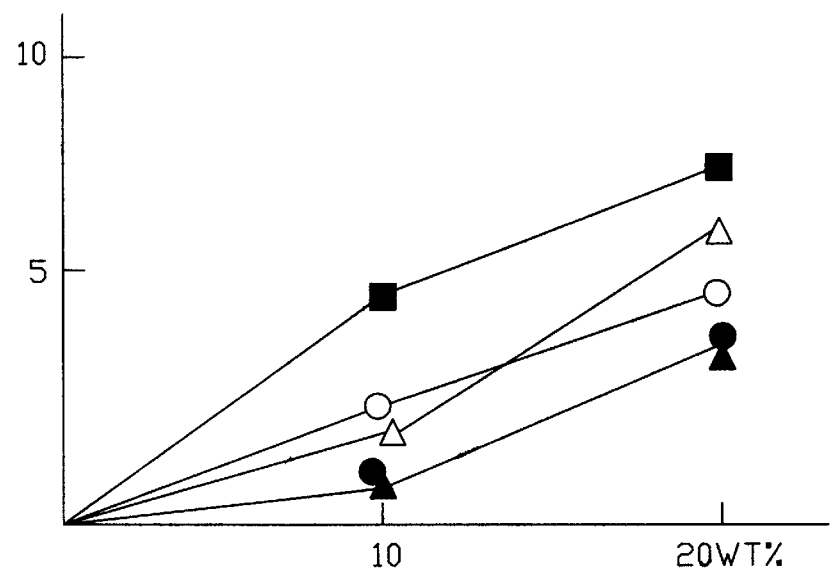
FIG. 2: DULLING IN COLOR OF PIGMENTS ADDING FLUID PARAFFIN

PIGMENT FOR SHIELDING OF ULTRAVIOLET RADIATION

BACKGROUND OF THE INVENTION

This invention relates to a pigment for shielding of ultraviolet radiation, and more particularly, to a pigment obtained by coating the surfaces of particles of a flaky powder with particles of zinc oxide and of barium sulfate for shielding of, among others, UV-A, a process for manufacturing the same, and the use thereof.

The amount of ultraviolet radiation of a wavelength range of 290 to 400 nm on the ground of the earth comprises about 6% of the light of the sun, of which about 0.5% has a relatively short wavelength in the range of 290 to 320 nm (hereinafter referred to as UV-B), while about 5.5%, or the greater part thereof, has a relatively long wavelength in the range of 320 to 400 nm (UV-A). UV-A passes clouds and window glass more easily because of its long wavelength than ultraviolet radiation having a short wavelength, and human skin is exposed to more UV-A in daily life, and UV-A penetrates into the skin tissue. While UV-B is scattered or absorbed on the surface of the skin and causes sunburn, or like inflammation to the skin, UV-A reaches the inner layer of the skin, and is said to produce in the skin tissue a radical causing aging of the skin by light, such as wrinkling, loosening, and a reduction of elasticity, exerting an adverse effect on the cell membranes, and genes. When intercepting ultraviolet radiation, therefore, it is not sufficient to think merely of shielding of the whole range of ultraviolet radiation, but it is of greater importance and interest to shield UV-A (Journal of Cosmetic Technology, 31, No. 1, pp. 14–30, 1997).

As materials having the power of shielding of ultraviolet radiation, there are, for example, known and commercially available metal oxides such as fine titanium oxide (see e.g. Japanese Patent Publication No. Sho 47-42502), fine iron oxide (see e.g. Japanese Patent Laid-open No. Hei 5-279235), fine zinc oxide (see e.g. Japanese Patent Laid-open No. Sho 60-231607), fine cerium oxide (see e.g. Japanese Patent Laid-open No. Hei 2-823312 and benzotriazole-based, or other organic agents for absorbing ultraviolet radiation. These commercially available agents for shielding of or absorbing ultraviolet radiation have, however, a number of problems including an insufficient shielding power for ultraviolet radiation and a limited scope of use, as will be pointed out below.

Fine titanium oxide, for example, has a low power of absorbing UV-A, and is required to have a larger particle diameter to exhibit shielding UV-A by scattering effect, but its larger particles lose transparency and have a higher degree of whiteness, thereby limiting the scope of its use. Fine iron oxide has a limited scope of use, since it is inferior in its power to shield of ultraviolet radiation versus any other metal oxide, and has a brown color. Fine zinc oxide has a high shielding power for ultraviolet radiation, but its high agglomeration property presents an obstacle to its use. It is necessary to use a special dispersing apparatus having a strong stirring force to disperse zinc oxide into primary particles having a diameter which enables it to shield ultraviolet radiation most effectively, but even if it may be divided into primary particles, it easily agglomerates again.

Fine cerium oxide is so expensive that it can hardly be used except for special purposes.

Benzotriazole-based, and other organic ultraviolet radiation absorbing agents have high absorbing power for ultraviolet radiation, but as they are organic compounds, they are basically lacking in stability, and cannot be expected to produce durable effects. Moreover, the use of any organic ultraviolet radiation absorbing agent as an additive to cosmetics is very strictly restricted from the standpoint of safety.

SUMMARY OF THE INVENTION

The invention provides a pigment for shielding of ultraviolet radiation, said pigment being obtained by coating a flaky (i.e., platelet-shaped) powder with particles of zinc oxide and barium sulfate. The pigment has a high power for shielding from ultraviolet radiation, particularly UV-A, while zinc oxide agglomerates less than prior art pigments. The ultraviolet radiation shielding pigment, when added to cosmetics, exhibits high extensibility (i.e., spreadability on the skin) and adhesiveness, basic properties required of cosmetics.

The invention therefore provides a pigment for shielding of ultraviolet radiation, which pigment comprises a flaky powder having particle surfaces coated with particles of barium sulfate having an average diameter of 0.1 to 2.0 microns, and with needle crystal (i.e., needle-shaped) particles of zinc oxide having an average major-axis (i.e., long axis) diameter of 0.05 to 1.5 microns. Barium sulfate is essentially platelet-shaped, and the diameter refers to the long axis. The needle type particle of ZnO is produced by the method of precipitating the dissolved zinc sulfate on the $BaSO_4$ coated mica using sodium hydroxide solution.

The invention also provides a process for manufacturing a pigment for shielding of ultraviolet radiation, which process comprises suspending a flaky powder in water to form a suspension; dropping (a) a water-soluble barium compound, and (b) a solution containing a higher chemical stoichiometric equivalent ratio of sulfate ions than barium ions in (a), into the suspension in such a way as either dropping (b) after adding an appropriate amount of (a), or dropping (a) and (b) simultaneously, whereby the particles of the flaky powder in the suspension are coated with particles of barium sulfate; dropping (c) a water-soluble zinc compound, and (d) a basic solution into the suspension in such a way as either dropping (d) after adding an appropriate amount of (c), or dropping (c) and (d) simultaneously, whereby the particles of the flaky powder are coated with the hydride or carbonate of zinc, collecting the coated particles by filtration; washing them; drying them; and calcining them.

The invention further provides a cosmetic, paint, or plastic resin material containing an appropriate amount of a pigment for shielding of ultraviolet radiation as defined above.

The ultraviolet radiation shielding pigment of this invention which comprises a flaky powder having particle coated with particles of barium sulfate having a specific diameter and needle crystal particles of zinc oxide has a high shielding power for ultraviolet radiation, particularly UV-A, and if it is used in a cosmetic, it is excellent not only in extensibility and adhesiveness, but also in resistance to color dulling, properties required of cosmetics.

The flaky powder which is used for the purpose of this invention may, for example, be mica, sericite, talc or kaolin having a particle diameter of 0.5 to 100 microns, and is usually mica (muscovite). A suspension is prepared by suspending, e.g., 5 to 20 parts by weight of such flaky powder in 100 parts by weight of water. The suspension is heated to, e.g., at least 50° C., preferably about 60–80° C., under stirring, and is then subjected to A: coating with particles of barium sulfate, and B: coating with zinc oxide, as will now be described.

A: Coating with Particles of Barium Sulfate

Either of two methods as described at (1) and (2) below can be employed for coating the flaky powder in the suspension with particles of barium sulfate.

(1) An appropriate amount of a water-soluble barium compound (a) is added to the suspension heated to about 60–80° C., and dissolved therein under stirring, and a separately prepared solution containing sulfate ions (b) is thereafter dropped into the suspension;

(2) An aqueous solution (a-1) is prepared from an appropriate amount of water-soluble barium compound (a), and the solution (a-1) and the above solution (b) are dropped simultaneously into the suspension heated to about 60–80° C., with stirring.

Examples of the water-soluble barium compound (a) or (a-1) include its chloride, nitrate and hydroxide. Examples of the source of sulfate ions (b) include sulfuric acid, sodium sulfate and potassium sulfate, the solution contains a higher chemical stoichiometric equivalent ratio of sulfate ions than the barium ions in (a).

B: Coating with Particles of Zinc Oxide

Either of two methods as described at (1) and (2) can be employed for coating with particles of zinc oxide.

(1) An appropriate amount of a water-soluble zinc compound (c) is added to, and dissolved in the suspension as obtained by A above, and a separately prepared basic solution (d) is thereafter dropped in the suspension, so that it may have a pH of 7 or above, and preferably 8 or above.

(2) An aqueous solution (c-1) is prepared from an appropriate amount of a water-soluble zinc compound (c), and the solutions (c-1) and (d) are dropped simultaneously into the suspension as obtained by A above, while it is kept at a pH of 7 or above.

Customary methods are employed for separating solid matter by filtration from the suspension obtained by either method (1) or (2) and containing the flaky powder coated with particles of barium sulfate and the hydride or basic carbonate of zinc, and barium sulfate and the hydride or basic carbonate of zinc, and for washing, drying and calcining it to obtain a pigment coated with particles of barium sulfate and of zinc oxide. Calcining is performed at a temperature of 500–900° C., and preferably at 600–800° C. At any temperature below 500° C., zinc fails to be completely oxidized, or its oxidation takes place at an undesirably low speed. At any temperature above 900° C., the particles coating the flaky particle surfaces undesirably undergo sintering to become larger in diameter than expected, or eventually agglomerate into larger masses.

Examples of the water-soluble zinc compound (c) or (c-1) are its chloride, sulfate and acetate. Examples of the basic substance in (d) are sodium hydroxide, potassium hydroxide, sodium carbonate, potassium carbonate, sodium hydrogen carbonate and potassium hydrogen carbonate.

The selection of the method (1) or (2) in each of A and B depends on the size of the coating particles as intended. If large coating particles are desired, for example, the method (2) (hereinafter referred to as the simultaneous dropping method) is suitable, while the method (1) is suitable if fine particle coating is desired. Apart from the coating method as discussed, the factors which determine the size of the particles of barium sulfate and zinc oxide include the temperature of the suspension, the shape of the reaction vessel employed, the shape of the stirring blade employed, and the stirring speed. The particles tend to have a smaller diameter if, for example, a lower temperature is employed, or if a higher stirring speed is employed, or if the reaction vessel is provided with a baffle, or if a higher dropping speed is employed. It is, therefore, advisable to select these conditions so that they may be suitable for the intended particle diameter. It is, of course, also possible to employ a combination of the method (1) in A and the method in B, or of the method (2) in A and the method (1) in B.

The barium sulfate particles prevent the agglomeration of the zinc oxide particles, and also exhibit their advantages in giving a cosmetic adhesiveness and extensibility on the skin as its important properties. The zinc oxide particles are a substance having a high power of shielding of ultraviolet radiation, and more particularly, UV-A, and in order that their excellent power may further be raised, or may not be lowered, the barium sulfate particles preferably have their average diameter controlled within the range of 0.1 to 2.0 microns. If their average diameter is smaller than 0.1 micron, the pigment has a lower degree of extensibility on the skin, and if it is larger than 2.0 microns, the pigment has a lower degree of transparency. The zinc oxide particles are of needle crystals, and preferably have an average major-axis diameter of 0.05 to 1.5 microns. If it is smaller than 0.05 micron, the pigment has a lower degree of extensibility on the skin, and if it is larger than 1.5 microns, the pigment has a lower power of shielding of ultraviolet radiation.

The coating amount of the barium sulfate particles is the minimum as required for lowering the agglomeration of the zinc oxide particles and, when used in a cosmetic, for giving it adhesiveness and extensibility on the skin, and is preferably 10 to 50 parts by weight relative to 100 parts by weight of flaky powder. If the amount is less than 10 parts by weight, the pigments may not exhibit satisfactory extensibility on the skin, and if the amount is more than 50 parts by weight, the pigments may not exhibit any greatly improved extensibility.

On the other hand, the zinc oxide particles are employed for shielding of UV-A, and for that purpose, it is preferable to employ the maximum possible amount thereof. Accordingly, the coating amount of the zinc oxide particles is preferably at least larger than that of the barium sulfate particles, and is more preferably 50 to 200 parts by weight relative to 100 parts by weight of flaky powder. If it is less than 50 parts by weight, they may not effectively shield UV-A, and if it is more than 200 parts by weight, the coating particles may agglomerate on the particle surfaces of the flaky powder and thereby fail to be of the desired size, or cause the particles of the flaky powder to agglomerate, or even fail to coat the particles of the flaky powder, depending on the chemical nature of the surfaces of the latter. Preferably, the molar ratio of $BaSO_4/ZnO$ is at least 0.03.

If the total amount of the barium sulfate and zinc oxide relative to the flaky powder exceeds the range as stated above, the particles may undergo agglomeration, or solidification to the extent that no primary particles may be obtained even by crushing, or otherwise.

There is, thus, obtained a pigment for shielding of ultraviolet radiation which comprises a flaky powder having particle surfaces coated with particles of barium sulfate having an average diameter of, e.g., 0.1 to 2.0 microns and needle crystal particles of zinc oxide having an average major-axis diameter of, e.g., 0.05 to 1.5 microns.

The ultraviolet radiation shielding pigment of this invention exhibits an outstanding power for shielding of ultraviolet radiation when mixed in a cosmetic, paint, or plastic material, as stated above. It has a particularly high power for shielding of UV-A as required of a cosmetic, exhibits good extensibility and adhesiveness on the skin, hardly has its color dulled when mixed with a body pigment, such as talc or mica, or oil, and is suitable for use in a foundation.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding Japanese Application No. 97-192021, filed Jul. 3, 1997 is hereby incorporated by reference.

EXAMPLES

Example 1

A suspension was prepared by suspending 150 g of fine muscovite particles having a diameter of 1 to 15 microns in 1.5 liters of water, and heated to about 80° C., and 50.7 g of barium hydroxide were added to it under stirring. Then, an aqueous solution of sulfuric acid having a concentration of 10% by weight was dropped at a rate of 2 ml/min. into the suspension under stirring until it had a pH of 3. Thereafter, its stirring was continued for about 10 minutes, and 662.5 g of zinc sulfate were added, and after about 10 minutes of stirring, a 32% by weight aqueous solution of sodium hydroxide was dropped into the suspension at a rate of 5 ml/min. until it had a pH of 8.5. Solid matter was separated from the suspension by filtration, washed, dried at about 105° C. for 15 hours, and calcined at 700° C. As a result, there was obtained an ultraviolet radiation shielding pigment in which 100 parts by weight of fine muscovie particles were coated with 25 parts by weight of barium sulfate particles and 125 parts by weight of zinc oxide particles. Its examination by a SEM revealed that the barium sulfate particles had an average diameter of about 0.3 micron, while the zinc oxide particles in needle crystal form had an average major-axis diameter of about 0.2 micron.

The pigment as obtained showed good extensibility and adhesiveness on the skin, and did not show any appreciable dulling in color when mixed with oil.

Example 2

A suspension was prepared by suspending 150 g of fine muscovite particles having a diameter of 1 to 15 microns in 1.5 liters of water, and heated to about 80° C., and 507 g of a 10% by weight aqueous solution of barium hydroxide were added to it under stirring, so that the suspension might have a pH of 8.5, and an aqueous solution of sulfuric acid having a concentration of 30% by weight was dropped therein at a rate of 7.5 ml/min. Then, after 30 minutes of stirring, 2208 g of a 30% by weight aqueous solution of zinc sulfate, and a 32% by weight aqueous solution of sodium hydroxide were dropped at a rate of 7.5 ml/min. into the suspension under stirring, while it was maintained at a pH of 8.5. Then, after 10 minutes of stirring, solid matter was separated from the suspension by filtration, washed, dried at about 105° C. for 15 hours, and calcined at 700° C. There was, thus, obtained an ultraviolet radiation shielding pigment in which 100 parts by weight of muscovite were coated with 25 parts by weight of barium sulfate particles and 125 parts by weight of zinc oxide particles. Its examination by a SEM revealed that the barium sulfate particles had an average diameter of about 1.5 microns, while the zinc oxide particles in needle crystal form had an average major-axis diameter of about 0.8 micron.

The pigment as obtained showed good extensibility and adhesiveness on the skin, and did not show any appreciable dulling in color when mixed with oil.

Comparative Example 1

A suspension was prepared by suspending 150 g of fine muscovite particles having a diameter of 1 to 15 microns in 1.5 liters of water, and heated to about 80° C., and 530 g of zinc sulfate were added to it under stirring. A 32% by weight aqueous solution of sodium hydroxide was dropped into the suspension at a rate of 5 ml/min. until it had a pH of 8.5. Then, after one hour of stirring, solid matter was separated from the suspension by filtration, washed, dried at about 105° C. for 15 hours, and calcined at 700° C.

As a result, there was obtained a pigment in which 100 parts by weight of muscovite were coated with 100 parts by weight of zinc oxide particles. Its examination by a SEM revealed that the zinc oxide particles in needle crystal form had an average major-axis diameter of about 0.2 micron.

The pigment as obtained was inferior to the pigment of Example 1 in extensibility and adhesiveness on the skin, and was inferior to those of Examples 1 and 2 in its power of shielding of ultraviolet radiation.

Comparative Example 2

A pigment in which 100 parts by weight of muscovite were coated with 40.6 parts by weight of barium sulfate and 15 parts by weight of zinc oxide (Example 6 in Japanese Patent Publication No. Hei 2-42388). This pigment was inferior to the pigments of Examples 1 and 2 in its power of shielding of ultraviolet radiation. It was also inferior to Example 1 in its resistance to color dulling.

Testing of the Power of Shielding of Ultraviolet Radiation
Preparation of Test Samples:

A test sample was prepared by admixing 0.3 g of each of the pigments according to Examples 1 and 2 and Comparative Examples 1 and 2 in 9.7 g of a medium ink based on a vinyl chloride resin to form a dispersion, applying the dispersion onto a glass plate by an applicator having a thickness of 120 microns, and drying it.

Method of Measuring Ultraviolet Radiation Transmittance:

A spectrophotometer (Model 228 of Hitachi) was used for examining each test sample for its transmittance of radiation having a wavelength of 200 to 700 nm (see FIG. 1). The ordinate axis represents the transmittance (%), while the abscissa axis represents the wavelength (nm). The powders as obtained in Examples 1 and 2 showed a low transmittance of radiation in the ultraviolet wavelength range (up to 400 nm) and the UV-A range, as compared with the products of Comparative Examples 1 and 2, and moreover, showed a minimum point of transmittance considered as absorption in the UV-A range. These results confirmed that the pigments of this invention had a high power of shielding of ultraviolet radiation.

[Testing on color dullness]

The pigment as prepared in each of the above Examples and Comparative Examples was mixed with liquid paraffin, and the hue which it presented in the mixture was compared with its original hue by a calorimeter (CR-300 of Minolta) as a measure of its color dullness having an important factor in the preparation of a cosmetic containing it. The results are shown in FIG. 2. In FIG. 2, the ordinate axis, $\Delta E^*$, represents the color difference as calculated by the following equation from the L value (lightness), the a value (red or green index) and the b value (yellow or blue index), while the abscissa axis represents the amount (%) of liquid paraffin in the mixture.

$$\Delta E^* = \sqrt{\Delta L^2 + \Delta a^2 + \Delta b^2}$$ [Equation 1]

As a result, it was confirmed that the pigment of Example 1 was more resistant to color dulling than that of Comparative Example 2 and a micaceous body pigment, and was suitable as a pigment for cosmetics.

Each of the pigments as prepared in the above Examples and Comparative Examples and mica were examined for their absorption of linseed oil. The results are shown in Table 1. The results confirmed that the pigments of Examples 1 and 2 absorbed a smaller amount of oil than the pigment of Comparative Example 1 not coated with barium sulfate, and were satisfactory in moldability when forming a cake in preparing a cosmetic, such as a compact powder.

TABLE 1

Absorption of oil by pigments

| Pigment | Amount of oil absorbed (ml/100 g) |
|---|---|
| Example 1 | 81 |
| Example 2 | 55 |
| Comparative Example 1 | 97 |
| Comparative Example 2 | 65 |
| Mica-M* | 53 |

*: A micaceous body pigment of Merck

The following is a description of a few examples of the use of the ultraviolet radiation shielding pigment according to the invention.

Example 1 of Use (Compact Powder)

| Composition | |
|---|---|
| Ultraviolet radiation shielding pigment according to Example 1 or 2: | 25 parts by weight |
| Color pigment: | 5 parts by weight |
| Lanolin: | 3 parts by weight |
| Isopropyl myristate: | Balance |
| Magnesium stearate: | 2 parts by weight |
| Talc: | 50 parts by weight |

[0026]

Example 2 of Use (Automobile Paint)

| Composition | |
|---|---|
| Composition A (acrylmelamine resin): | |
| Acrydic 47-712: | 70 parts by weight |
| Super Beccamine G821-60: | 30 parts by weight |

| Composition B | |
|---|---|
| Ultraviolet radiation shielding pigment according to Example 1 or 2: | 10 parts by weight |
| Pearl pigment: | 10 parts by weight |

| Composition C (thinner for acrylmelamine resin) | |
|---|---|
| Ethyl acetate: | 50 parts by weight |
| Toluene: | 30 parts by weight |

| Composition C (thinner for acrylmelamine resin) | |
|---|---|
| n-butanol: | 10 parts by weight |
| Solvesso #150: | 40 parts by weight |

A mixture of Compositions A and B is diluted with Composition C to form a dilution having a viscosity suitable for spray coating (12 to 15 seconds with a Ford Cup #4), and it is sprayed to form a base coat layer.

Example 3 of Use (Plastic Composition)

| Composition | |
|---|---|
| High-density polyethylene resin (pellets): | 100 parts by weight |
| Ultraviolet radiation shielding pigment according to Example 1 or 2: | 1 part by weight |
| Magnesium stearate: | 0.1 part by weight |
| Zinc stearate: | 0.1 part by weight |

The pellets of the above composition are dry blended, and injection molded.

BRIEF DESCRIPTION OF THE DRAWINGS

FIG. 1 is a graph comparing the pigments of Examples 1 and 2 and Comparative Examples 1 and 2 with respect to their transmittance of ultraviolet radiation having a wavelength in the range of 200 to 700 nm;

FIG. 2 is a graph showing the results of the tests conducted to examine the dulling in color of each of the pigments according to Examples 1 and 2 and Comparative Examples 1 and 2.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A pigment for ultraviolet radiation shielding comprising a flaky powder having surfaces coated with particles of barium sulfate and needle crystal particles of zinc oxide, wherein the barium sulfate particles have an average diameter of 0.1 to 2.0 microns and the zinc oxide particles are needle crystals having an average major-axis diameter of 0.05 to 1.5 microns.

2. A pigment according to claim 1, wherein the flaky powder is mica, sericite, or talc.

3. A pigment as claimed in claim 2, wherein the amount of barium sulfate is less than that of zinc oxide.

4. A pigment as claimed in claim 2, wherein the amount of barium sulfate is from 10 to 50 parts by weight, relative to 100 parts by weight of the flaky powder.

5. A pigment as claimed in claim 2, wherein the amount of zinc oxide is from 50 to 200 parts by weight, relative to 100 parts by weight of the flaky powder.

6. A pigment for ultraviolet radiation shielding comprising a flaky powder having surfaces coated with particles of barium sulfate and needle crystal particles of zinc oxide, wherein the amount of barium sulfate is less than that of said zinc oxide, and is 10 to 50 parts by weight, and the amount of said zinc oxide is 50 to 200 parts by weight, relative to 100 parts weight of said flaky powder.

7. A pigment according to claim 6, wherein the flaky powder is mica, sericite, talc or kaolin.

8. A process for manufacturing a pigment for ultraviolet radiation shielding, said pigment being coated with particles of barium sulfate have an average diameter of 0.1 to 2.0 microns, and needle crystal particles of zinc oxide, having an average major-axis diameter of 0.05 to 1.5 microns, which comprises suspending a flaky powder in water to form a suspension;

dropping (a) a water-soluble barium compound, and (b) a solution containing a higher than chemical stoichiometric equivalent ratio of sulfate ions with respect to barium ions in (a), into said suspension by either dropping (b) after adding (a), or dropping (a) and (b) simultaneously, whereby the particles of said flaky powder in said suspension are coated with particles of barium sulfate;

dropping (c) a water-soluble zinc compound, and (d) a basic solution into said suspension by either dropping (d) after adding (c), or dropping (c) and (d) simultaneously, whereby said particles of said flaky powder are coated with a hydride or carbonate of zinc, and washing, drying, and calcining the coated particles.

9. A process as claimed in claim 8, wherein the step of suspending a flaky powder in water further comprises heating the suspension to at least 50° C.

10. A process as claimed in claim 8, wherein the step of calcining the pigment occurs at a temperature of from 500 to 900° C.

11. A pigment for ultraviolet radiation shielding comprising a flaky powder having particle surfaces coated with particles of barium sulfate and needle crystal particles of zinc oxide, wherein the barium sulfate particles have an average diameter of 0.1 to 2.0 microns and the zinc oxide particles are needle crystals having a major-axis diameter of 0.05 to 1.5 microns, the amount of barium sulfate is less than that of the zinc oxide, and the amount of barium sulfate is 10 to 50 parts by weight relative to 100 parts by weight of the flaky powder, and the amount of zinc oxide is 50 to 200 parts by weight relative to the 100 parts by weight of the flaky powder, prepared by:

suspending a flaky powder in water to form a suspension and heating the suspension to at least 50 degrees C;

dropping a water-soluble barium compound (a) and a solution (b) containing a higher than chemical stoichiometric equivalent ratio of sulfate ions with respect to barium ions in (a) into said suspension by either dropping (b) after adding (a), or dropping (a) and (b) simultaneously;

dropping a water-soluble zinc compound (c) and a basic solution (d) into the suspension by either dropping (d) after adding (c) or dropping (c) and (d) simultaneously, and;

calcining the pigment at a temperature of from 500 to 900 degrees C after washing and drying.

12. A cosmetic, paint, or plastic material containing a pigment as set forth in claim 1.

13. A cosmetic, paint, or plastic material containing a pigment as set forth in claim 2.

14. A cosmetic, paint, or plastic material containing a pigment as set forth in claim 6.

15. A cosmetic, paint, or plastic material containing a pigment as set forth in claim 7.

* * * * *